United States Patent
Veillette et al.

(10) Patent No.: US 7,672,723 B2
(45) Date of Patent: Mar. 2, 2010

(54) IMPLANTABLE MEDICAL DEVICE FOR BIVENTRICULAR STIMULATION

(75) Inventors: Benoit Veillette, Portland, OR (US); Jim Hess, Aloha, OR (US); David Wiggins, Tualatin, OR (US)

(73) Assignee: Biotronik CRM Patent AG, Baar (CH)

( * ) Notice: Subject to any disclaimer, the term of this patent is extended or adjusted under 35 U.S.C. 154(b) by 341 days.

(21) Appl. No.: 11/742,337

(22) Filed: Apr. 30, 2007

(65) Prior Publication Data

US 2008/0269817 A1 Oct. 30, 2008

(51) Int. Cl.
*A61N 1/36* (2006.01)
(52) U.S. Cl. .......................................................... 607/9
(58) Field of Classification Search ................... 607/7, 607/9
See application file for complete search history.

(56) References Cited

U.S. PATENT DOCUMENTS

| 6,611,714 B1 | 8/2003 | Mo |
| 2004/0077963 A1 | 4/2004 | Perschbacher et al. |
| 2006/0004418 A1 | 1/2006 | Stahmann et al. |
| 2007/0150010 A1* | 6/2007 | Stubbs et al. ................ 607/9 |
| 2008/0109041 A1* | 5/2008 | de Voir ........................... 607/7 |

FOREIGN PATENT DOCUMENTS

EP  1 038 548  9/2000

OTHER PUBLICATIONS

European Search Report, dated Aug. 31, 2009.

* cited by examiner

*Primary Examiner*—George Manuel
*Assistant Examiner*—Robert N Wieland
(74) *Attorney, Agent, or Firm*—Dalina Law Group, P.C.

(57) ABSTRACT

A heart stimulator for biventricular pacing comprises at least one stimulation pulse generator connected or connectable to a right ventricular or atrial stimulation electrode lead and a left ventricular or atrial electrode lead, respectively. The heart stimulator is adapted to generate right chamber stimulation pulses for a right atrium or ventricle and left chamber stimulation pulses for a left ventricle or atrium. A high rate protection unit connected to said stimulation pulse generator is adapted to trigger, upon any right or left chamber stimulation pulse, a protection time window having a predetermined duration in time and comprising an early part immediately followed by a late part. The protection unit is further adapted to only allow atrial or ventricular stimulation pulses in said early part of said protection time window and to suppress any atrial or ventricular stimulation pulse in said late part.

16 Claims, 3 Drawing Sheets

IMPLANTABLE MEDICAL DEVICE FOR BIVENTRICULAR STIMULATION

BACKGROUND OF THE INVENTION

1. Field of the Invention

The invention refers to implantable medical devices (IMDs) providing means for electrical stimulation of heart chambers and a high rate protection preventing excessive stimulation rates. The invention relates in particular to implantable cardiac pacemaker or an implantable cardioverter/defibrillator (ICD) for bi-ventricular stimulation.

2. Description of the Related Art

Implantable heart stimulators can be used for treating a variety of heart disorders like bradycardia, tachycardia or fibrillation by way of electric stimulation pulses delivered to the heart tissue, the myocardium. A strong enough stimulation pulse outside a heart chamber's refractory period leads to an excitation of the myocardium of that heart chamber, which in turn is followed by a contraction of the respective heart chamber.

Depending on the disorder to be treated, such a heart stimulator generates electrical stimulation pulses that are delivered to the heart tissue (myocardium) of a respective heart chamber according to an adequate timing regime. Delivery of stimulation pulses to the myocardium is usually achieved by means of an electrode lead that is electrically connected to a stimulation pulse generator inside a heart stimulator's housing and that carries a stimulation electrode in the region of its distal end. A stimulation pulse also is called a pace. Similarly, pacing a heart chamber means stimulating a heart chamber by delivery of a stimulation pulse.

Usually, a heart stimulator features separate stimulation generators for each heart chamber to be stimulated. Therefore, in a dual chamber pacemaker, usually an atrial and a ventricular stimulation pulse generator for generating atrial and ventricular stimulation pulses are provided. Delivery of an atrial or a ventricular stimulation pulse causing an artificial excitation of the atrium or the ventricle, respectively, is called an atrial stimulation event AP (atrial paced event) or a ventricular stimulation event VP (ventricular paced event), respectively.

In biventricular pacemakers both ventricles of a heart are paced.

Biventricular pacemakers are used for a cardiac re-synchronization therapy that shall synchronize right ventricular contraction and left ventricular contraction to improve the output of a heart exhibiting a cardiovascular disease. In particular, cardiac synchronization therapy is used to treat heart failure in patients with wide QRS complex that results from a delayed excitation of the left heart side. It is believed, that a main contributor to heart failure (the heart's inability to generate enough cardiac output) is an asynchronous mechanical contraction of the left and right side of the heart.

In a heart cycle, an excitation of the myocardium leads to depolarization of the myocardium that causes a contraction of the heart chamber. If the myocardium is fully depolarized, it is unsusceptible for further excitation and thus refractory. Thereafter, the myocardium repolarizes and thus relaxes and the heart chamber is expanding again. In a typical electrogram (EGM), depolarization of the ventricle corresponds to a signal known as "R-wave". The repolarization of the ventricular myocardium coincides with a signal known as "T-wave". Atrial depolarization is manifested by a signal known as "P-wave".

After a pace event, the cardiac tissue in the paced chamber is refractive for at least 125 ms. This means that another pace during this period will not have any effect. The tissue then repolarises until it reaches the resting state, typically no later than 270 ms after the pace. The phase between the time when the tissue is refractive and the time when it reaches the resting state is known as the vulnerable period that approximately coincides with a T-wave. A second pace event during this time may cause a potentially fatal tachycardia.

Cardiac rhythm management (CRM) devices are designed to avoid pacing in the vulnerable period. However, a fault could result in this undesired behaviour. As an example of such a fault, the crystal oscillator circuit could lock on a harmonic of the crystal. Another cause for pacing in the vulnerable period could be a modification of the CRM device configuration due to ambient radiation (soft error).

This issue is recognized to the extent that a European Standard for pacemakers (EN 45502-2-1:2003, section 16.4) mandates the following:

The design of the implantable pulse generator shall include a feature to limit the pulse rate in the event of a fault within the device (run-away protection).

Dual chamber devices implement a high-rate protection (HRP) circuit on each of the two chambers: atrium and ventricle. These HRP circuits use an independent time base and pre-vent consecutive pace events from occurring closer than a chosen interval, typically 270 ms.

SUMMARY OF THE INVENTION

It is an object of the invention to provide an implantable medical device that provides an improved high rate protection in bi-ventricular heart stimulators.

The inventors have recognized that extending the prior art high rate protection concepts known from dual chamber heart stimulators to cardiac resynchronization therapy (CRT) devices (biventricular heart stimulators) would mean independent HRP circuits for the right and left ventricles. However, this approach does not take into account the close coupling of the right and left ventricle. Stimulation of either the left or right ventricle will cause the entire ventricle to depolarize. Delivery of stimulation pulses to (Pacing of) either the left or right ventricle while the ventricle is in the vulnerable period may induce a potentially fatal tachycardia.

According to the present invention, the object of the invention is achieved by a heart stimulator for biventricular pacing of a heart, comprising:

at least one stimulation pulse generator being connected to or being connectable to a right ventricular stimulation electrode lead and a left ventricular electrode lead and being adapted to generate right ventricular stimulation pulses and left ventricular stimulation pulses to pace at least a right and a left ventricle of a heart, and a high rate protection unit, being connected to said stimulation pulse generator.

The high rate protection unit is adapted to respond to a generation of both, right- and left-ventricular stimulation pulses and to trigger a protection time window upon a ventricular stimulation pulse for either a right or a left ventricle, wherein said protection time window has a predetermined duration in time and comprises an early part and a late part immediately following the early part.

The high rate protection unit is further adapted to allow ventricular stimulation pulse for any ventricle in the early part of the protection time window and to suppress any ventricular stimulation pulse in said late part of said protection time window.

The high rate protection unit is further adapted to allow a single ventricular stimulation pulse for any ventricle in said early part of the protection time window and to suppress any further ventricular stimulation pulse in the early part.

Likewise, a method of pacing both ventricles of a heart is suggested, that comprises the steps of:

Triggering an early part of a protection time window upon delivery of ventricular stimulation pulse, Allowing one or more ventricular stimulation pulses during said early part of said protection time window, Starting a late part of said protection time window upon expiration of said early part of said protection time window, and Suppressing any ventricular stimulation pulse in said late part of said protection time window.

Preferably, the method only allows one single ventricular stimulation pulses during said early part of said protection time window, According to the invention the concept of high rate protection can be applied to a bi-atrial heart stimulator in an analogous manner.

The total duration of the protection time window preferably corresponds to the time duration between initiating excitation of myocardium returning of the myocardium to its resting state and thus is between 200 ms and 300 ms, preferably about 230 ms for young children and 270 ms for adults.

The duration of the early part of the protection time window preferably corresponds to the refractory period of myocardium after delivery of a stimulation pulse and thus is between 100 ms and 150 ms, preferably about 125 ms.

The high rate protection unit may be part of a control unit for scheduling of stimulation pulses.

Alternatively, the high rate protection unit could be formed by a high rate protection circuit that is independent from a circuit forming said control unit and that is connected to said control unit of said control unit in order to interoperate with said control unit.

It is to be appreciated that features of preferred embodiments of the invention may be combined in any useful manner thus arriving at further preferred embodiments of the invention not explicitly mentioned in this disclosure.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
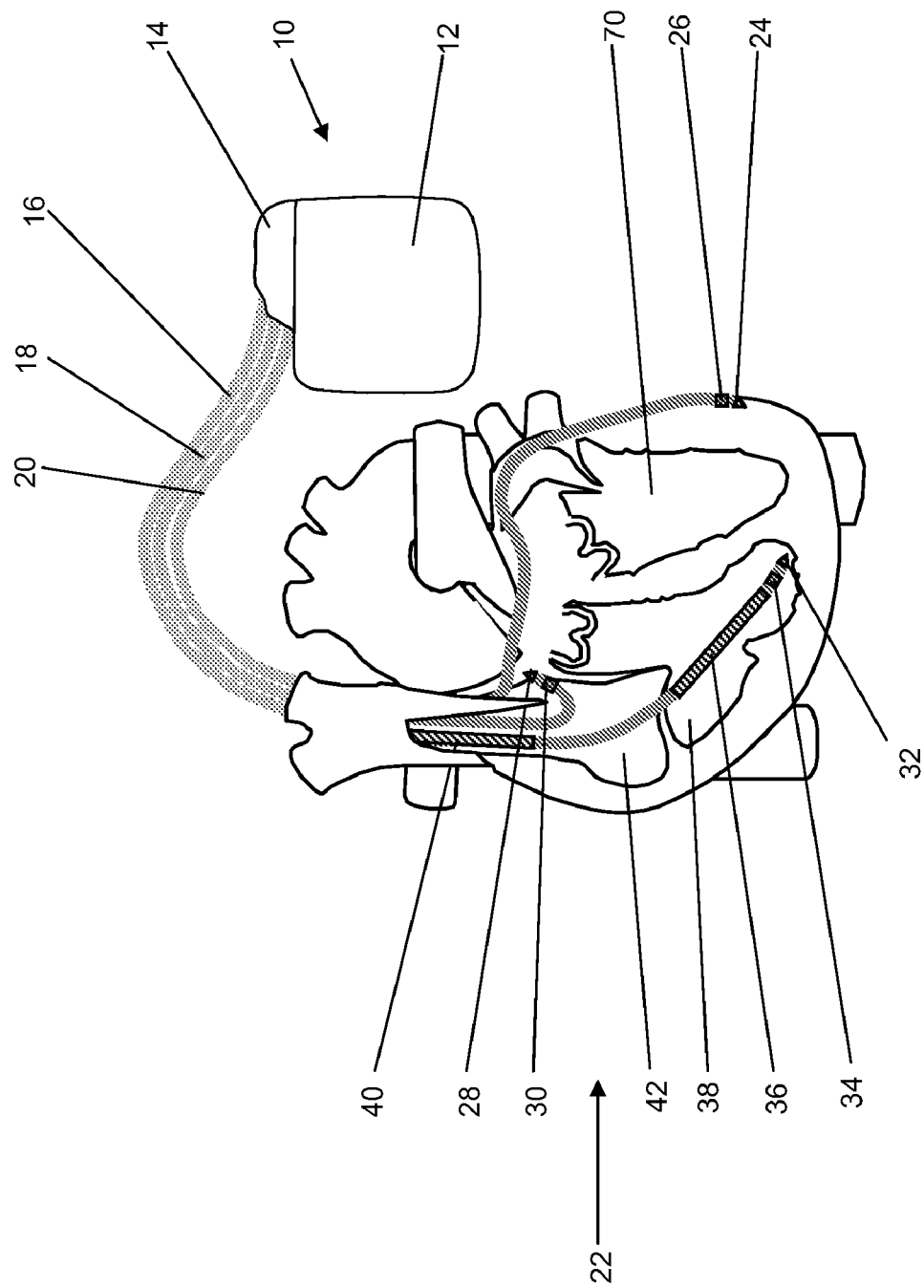
FIG. 1 shows a dual chamber pacemaker/atrial defibrillator/cardioverter connected to leads placed in a heart.

From FIG. 1 it is apparent that stimulator 10 comprises a case 12 and header 14.

The heart stimulator 10 is connected to three electrode leads, namely a right ventricular electrode lead for 16, a right atrial electrode lead 18 and a left ventricular electrode lead 20.

The left ventricular electrode lead 20 is designed to pass trough the coronary sinus of heart 22. A typical electrode suitable for use with heart stimulator 10 is the electrode lead corox+UP/BB by the applicant.

Left ventricular electrode lead 20 comprises a left ventricular tip electrode 24 at the distal end a left ventricular electrode lead 20 and a left ventricular ring electrode 26.

Atrial electrode lead 18 comprises a right atrial tip electrode 28 at the distal end of right atrial electrode lead 18 and a right atrial ring electrode 30.

The right ventricular electrode lead 16 comprises right ventricular tip electrode 32 at the distal end of right ventricular electrode lead 16 and a right ventricular ring electrode 34.

In order to illustrate, the heart stimulator 10 may be adapted to act as an implantable cardioverter/defibrillator (ICD) ventricular electrode lead 16 also exhibits a ventricular shock coil 36 for the delivery of defibrillation shocks to right ventricle 38 of heart 22 and an atrial shock coil 40 for the delivery of atrial defibrillation shocks to a right atrium 42 of heart 22.

Each electrode and shock coil of electrode leads 16 to 20 is separately connected to an electric circuit enclosed by case 12 of heart stimulator 10 by way of electrical contacts of a plaque (not shown) at the proximal end of each electrode lead 16 to 20 and corresponding contacts (not shown) in header 14 of heart stimulator 10.

Figure 2:
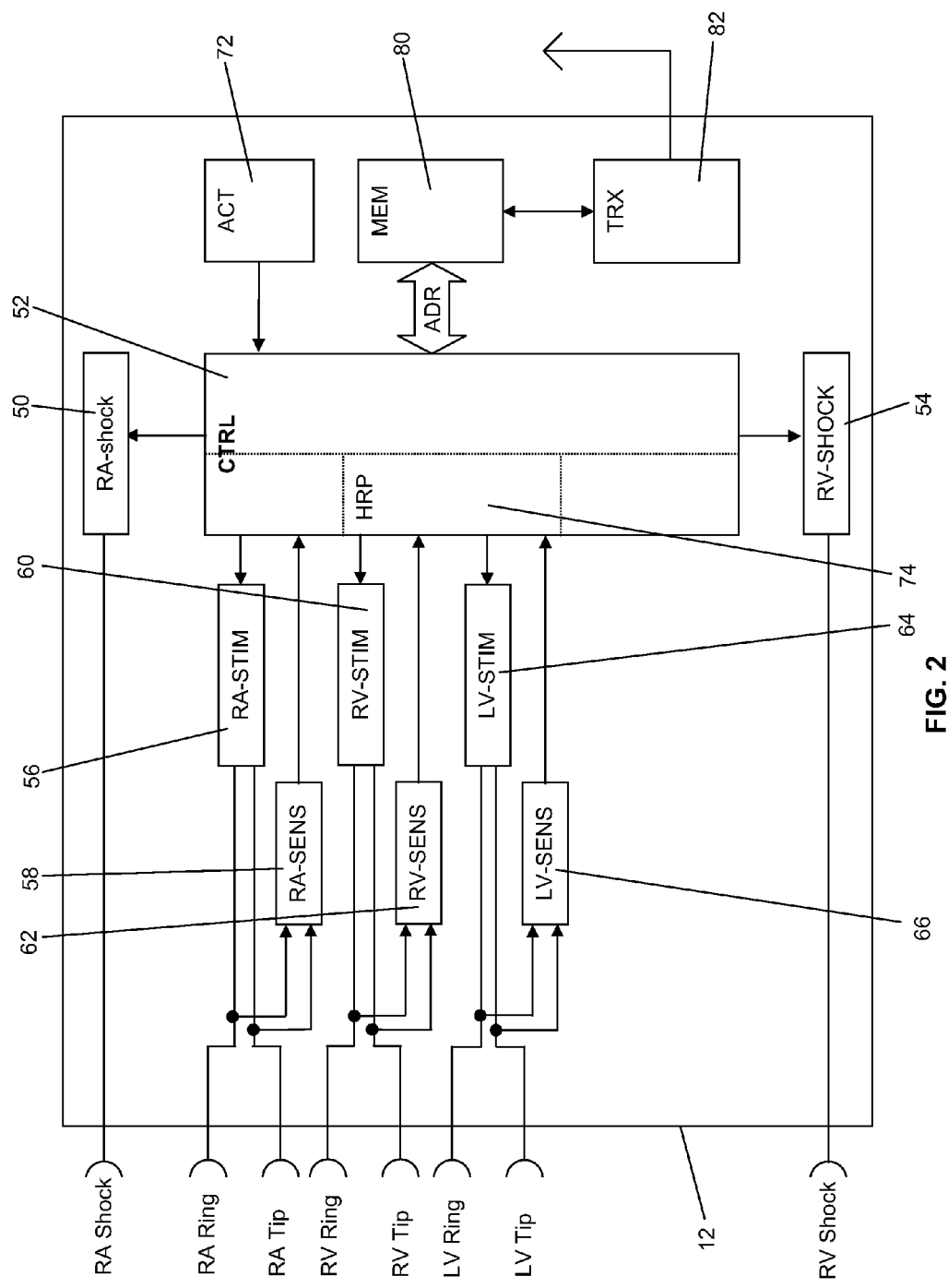
FIG. 2 is a block diagram of the device of FIG. 1.

Right atrial shock coil 40 is connected to right atrial shock generator 50 (see FIG. 2) that is controlled by a control unit 52 of heart stimulator 10.

Similarly right ventricular shock coil 36 is connected to a right ventricular shock generator 54 that is also connected to control unit 52.

Right atrial tip electrode 28 and right atrial ring electrode 30 are both connected to a right atrial stimulation pulse generator 56 and a right atrial sensing stage 58 that internal both connected to control unit 52.

Sensing stages are provided in order to be able to sense a contraction a heart chamber that naturally occurs without artificial stimulation and that is called intrinsic. An intrinsic excitation of a heart chamber results in characteristic electrical potentials that can be picked up via the sensing electrode and that can be evaluated by the sensing stage in order to determine whether an intrinsic excitation—called: intrinsic event—has occurred.

Separate sensing stages 58, 62 and 66 are provided for the right atrium RA 42, right ventricle RV 38 and left ventricle LV 70.

By means of a sensing stage for a heart chamber to be stimulated, the pacemaker is able to only trigger stimulation pulses when needed that is when no intrinsic excitation of the heart chamber occurs in time. Such mode of pacing a heart chamber is called demand mode. In the demand mode the pacemaker schedules an atrial or a ventricular escape interval that causes triggering of an atrial or ventricular stimulation pulse when the escape interval times out. Otherwise, if an intrinsic atrial or ventricular event is detected prior to time out of the respective atrial or ventricular escape interval, triggering of the atrial or ventricular stimulation pulse is inhibited. Such intrinsic (natural, non-stimulated) excitation is manifested by the occurrence of recognizable electrical signals that accompany the depolarization or excitation of a cardiac muscle tissue (myocardium). The depolarization of the myocardium is usually immediately followed by a cardiac contraction. For the purpose of the present application, depolarization and contraction may be considered as simultaneous events and the terms "depolarization" and "contraction" are used herein as synonyms.

Right atrial stimulation pulse generator 56 is adapted to generate atrial stimulation pulses of sufficient strength to cause an excitation of atrial myocardium by an electrical stimulation pulse delivered via right atrial tip electrode 28 and right atrial ring electrode 30. Preferably, means are provided to adapt the right atrial stimulation pulse strength to the stimulation threshold.

Right atrial sensing stage 58 is adapted to pick up myocardial potentials indicating an intrinsic atrial excitation that corresponds to a natural atrial contraction. By way of right atrial sensing stage 58, it is possible to stimulate the right atrium 42 of heart 22 in a demand mode wherein a right atrial stimulation pulse is inhibited if an intrinsic atrial event (intrinsic atrial excitation) is sensed by right atrial sensing stage 58 prior to expiration of an atrial escape interval.

In a similar manner, right ventricular ring electrode 34 and right ventricular tip electrode 32 are connected to right ventricular stimulation pulse generator 60 and to a right ventricular sensing stage 62 that in turn are connected to control unit 52. By way of right ventricular tip electrode 32, right ventricular ring electrode 34, right ventricular stimulation generator 60 and right ventricular sensing stage 62, right ventricular stimulation pulses can be delivered in a demand mode to the right ventricle 38 of heart 22.

In the same way left ventricular tip electrode 32 and left ventricular ring electrode 26 are connected to the left ventricular stimulation pulse generator 64 and the left ventricular sensing stage 66 that internal connected to control unit 52 and that allow for stimulating a left ventricle 70 of heart 22.

Triggering and inhibition of delivery of stimulation pulses to the right atrium, the right ventricle or the left ventricle is controlled by control unit 52 in a manner generally known to the man skilled in the art. The timing that schedules delivery of stimulation pulses if needed is controlled by a number of intervals, that at least partly may depend on a hemodynamic demand of a patient that is sensed by means of an activity sensor 72 that is connected to control unit 52. Activity sensor 72 allows for rate adaptive pacing wherein a pacing rate (the rate of consecutive ventricular stimulation pulses for a duration of consecutive atrial stimulation pulses) depends on a physiological demand of a patient that is sensed by a way of activity sensor 72. Activity sensor 72 serves for sensing the hemodynamic demand of a patient. Instead of a single activity sensor one or more alternative sensors may be provided for sensing the hemodynamic demand of a patient.

Details of rate adaptation are known to the man skilled in the art but need not to be explained in detail in this description.

Whereas an actual stimulation rate determines the timing from one (paced) heart cycle to another, intervals like an atrioventricular delay interval and an interventricular delay interval determine the timing within one heart cycle. Starting with an atrial event, the right ventricle would be excited (either intrinsically or paced) at the end of an atrioventricular delay interval. A left ventricular contraction should follow the right ventricular contraction at the end of an interventricular delay interval. This shall include the case, wherein the right ventricle and the left ventricle are excited the same time resulting in an interventricular delay interval duration of zero. Also, it is possible that the left ventricle is excited prior to the right ventricle resulting in an negative interventricular delay interval duration.

In any case, the atrioventricular delay interval duration and the interventricular delay interval duration need to be adapted to an individual heart in order to achieve an optimized cardiac output.

However, care has to be taken that none of the chambers of the heart is paced with too high a stimulation rate. As already pointed out before, this is usually achieved by means of a high rate protection unit that may comprises timer circuitry that is independent from other rate control units. Such a state of the art high rate protection may be provided with the atrial channel of pacemaker 10 and is not shown in the drawings.

Because of the close coupling of the right ventricle and the left ventricle, a special high rate protection unit HRP 74 is provided that provides for high rate protection in biventricular heart stimulators and protects both ventricular channels simultaneously.

Operation of the high rate protection unit HRP 74 is now illustrated with respect to FIGS. 3 and 4A to 4C.

The high rate protection unit 74 is a single biventricular circuit that considers two channels simultaneously. Thus, the high rate protection unit 74 has the effect that any pace in either the right or left ventricle requested at a time after a pace in either the right or left ventricle that is within the protection interval is blocked from stimulating the heart.

Figure 3:
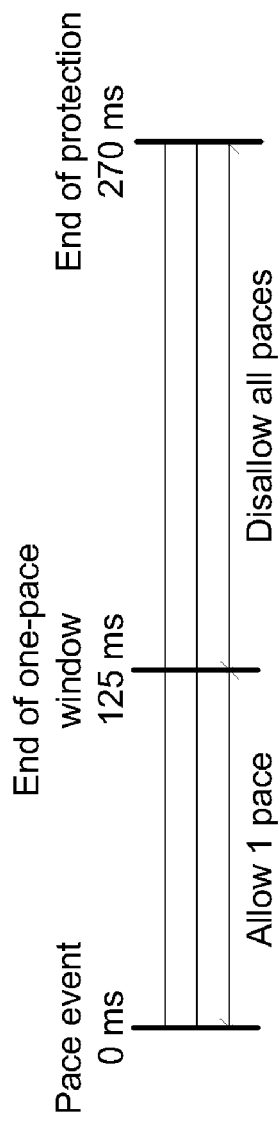
FIG. 3 is an illustration of a protection time window according to the invention.
Figure 4:
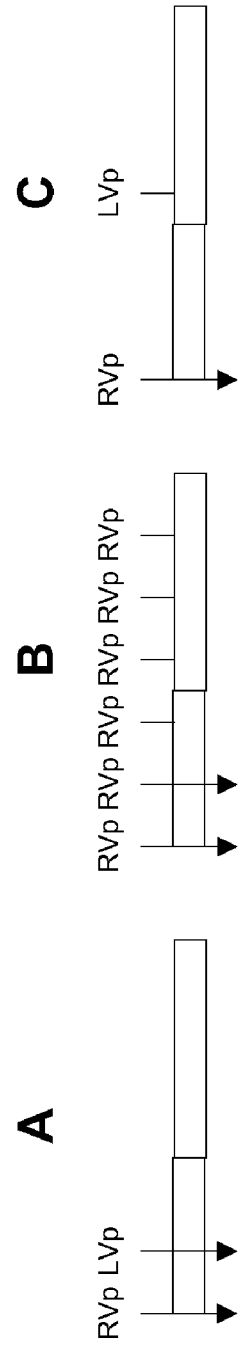
FIGS. 4A to C illustrate the effect of the protection time window in different scenarios.

The high rate protection unit 74 establishes a protection time window as illustrated in FIGS. 3 and 4. The protection time window comprises an early part forming a first interval and a late part forming a second interval, which immediately follows the first interval. The protection time window duration corresponds to the time when the tissue is known to have reached the resting state and is typically 270 ms. The high rate protection unit 74 is adapted to start the protection time window with a pace event (delivery of a stimulation pulse) in one heart chamber, e.g. the right ventricle. It controls delivery of stimulation pulses (paces) to this heart chamber as well as the other, corresponding heart chamber, e.g. the left heart ventricle.

To allow for resynchronization therapy, according to the preferred embodiment, a single pace occurring at a time within the first interval after the pace event triggering the protection time window will be allowed. Subsequent pace events within the protection window will be suppressed. However, more than one pace up to an unlimited number of paces could be allowed in alternative embodiments of the invention that are not subject of this description of a preferred embodiment but that shall into the scope of protection of the claims herein after.

The duration of this first interval corresponds to the minimum refractory period and is typically 125 ms. FIG. 3 illustrates the timing of the bi-ventricular high rate protection circuit that forms high rate protection unit 74. The protection time window 80 is started with a right ventricular pace event. An early part of the protection time window forms a first interval 82 that expires after 125 ms. During the first interval, a single pace can be delivered. For this reason the first interval is also called "one-pace window". A late part of the protection time window forms a second interval 84 that immediately follows the first interval and that expires at the expiration of the protection time window 80 about 270 ms after triggering the protection time window 80. During the second interval 84, the high rate protection unit 74 suppresses any ventricular stimulation pulse.

FIGS. 4A to 4C demonstrate the operation of the biventricular HRP circuit 74.

FIG. 4A shows the normal operation. The left ventricular pace (LVp) following a right ventricular pace (RVp) is allowed because it occurs before the end of the first interval 82 corresponding to the ventricle's refractory period and it is the first pace event within the first interval.

FIG. 4B shows the effect of a faulty system time base. Pace requests occur in rapid successions. The bi-ventricular high rate protection circuit only allows two paces including the pace triggering the high rate protection time window 80. Since the second scheduled pace event is within the first interval 82 it is allowed by high rate protection unit 74. Because the second scheduled pace event occurs in the ventricle's refractory period there is no harm to the patient.

Finally, FIG. 4C shows an abnormal intra-ventricular delay that leads to scheduling of a left ventricular pace event that would occur during a period of time that is likely to be the vulnerable phase of the ventricle and thus could induce a possibly lethal ventricular fibrillation. The high rate protection unit 74 is adapted to prevent triggering of such left ventricular pace since it occurs during the second interval 84 of the high rate protection window 80.

Although an exemplary embodiment of the present invention has been shown and described, it should be apparent to those of ordinary skill that a number of changes and modifications to the invention may be made without departing from the spirit and scope of the invention. In particular, it is possible to implement the features of the claimed high rate protection unit into state of the art implantable medical devices such as implantable pacemakers or implantable cardioverter/defibrillator. This invention can readily be adapted to such devices by following the present teachings. All such changes, modifications and alterations should therefore be recognized as falling within the scope of the present invention.

What is claimed is:

1. A heart stimulator for biventricular pacing of a heart, comprising:
    at least one stimulation pulse generator being connected to or being connectable to a right ventricular or atrial stimulation electrode lead and a left ventricular or atrial electrode lead, respectively, and being configured to generate right chamber stimulation pulses for a right atrium or a right ventricle and left chamber stimulation pulses for a left ventricle or left atrium, respectively, to pace at least a right and a left ventricle or atrium of a heart;
    a high rate protection unit, being at least indirectly connected to said stimulation pulse generator;
    said high rate protection unit being configured to trigger a protection time window upon any right or left chamber stimulation pulse, wherein said protection time window has a predetermined duration in time and comprises an early part and a late part immediately following said early part and wherein a total duration of the protection time window corresponds to a time duration between initiating excitation of myocardium and returning of the myocardium to its resting state;
    wherein said high rate protection unit is further configured to
        only allow atrial or ventricular stimulation pulses in said early part of said protection time window; and,
        suppress any atrial or ventricular stimulation pulse, respectively, in said late part of said protection time window.

2. The heart stimulator of claim 1, wherein said high rate protection unit is further configured to allow a single stimulation pulse for any atrium or ventricle in said early part of said protection time window and to suppress any further stimulation pulse in said early part.

3. The heart stimulator of claim 1, wherein said total duration of said protection time window is between 200 ms and 300 ms.

4. The heart stimulator of claim 3, wherein said total duration of said protection time window is about 270 ms.

5. The heart stimulator of claim 1, wherein said duration of said early part of said protection time window corresponds to a refractory period of myocardium after delivery of a stimulation pulse.

6. The heart stimulator of claim 5, wherein said duration of said early part of said protection time window is between 100 ms and 150 ms.

7. The heart stimulator of claim 6, wherein said duration of said early part of said protection time window is about 125 ms.

8. The heart stimulator of claim 1, wherein said heart stimulator comprises a control unit for scheduling of stimulation pulses and wherein said high rate protection unit is part of said control unit.

9. The heart stimulator of claim 1 wherein said heart stimulator comprises a control unit for scheduling of stimulation pulses and wherein said high rate protection unit is formed by a high rate protection circuit that is independent from a circuit forming said control unit and that is connected to said control unit in order to interoperate with said control unit.

10. A method of pacing both ventricles of a heart, said method comprising:
    triggering an early part of a protection time window upon delivery of a an atrial or a ventricular stimulation pulse;
    allowing one or more atrial or ventricular stimulation pulses, respectively, during an early part of said protection time window;
    starting a late part of said protection time window upon expiration of said early part of said protection time window;
    suppressing any atrial or ventricular stimulation pulse, respectively, in said late part of said protection time window; and,
    utilizing a total duration for the protection time window that corresponds to a time duration between initiating excitation of myocardium and returning of the myocardium to its resting state.

11. The method of claim 10, wherein only one single atrial or ventricular stimulation pulse is allowed during said early part of said protection time window.

12. The method of claim 10, wherein said total duration of said protection time window is between 200 ms and 300 ms.

13. The method of claim 12, wherein said total duration of said protection time window is about 270 ms.

14. The method of claim 10, wherein said duration of said early part of said protection time window corresponds to a refractory period of myocardium after delivery of a stimulation pulse.

15. The method of claim 14, wherein said duration of said early part of said protection time window is between 100 ms and 150 ms.

16. The method of claim 15, wherein said duration of said early part of said protection time window is about 125 ms.

* * * * *